US006708136B1

(12) United States Patent
Lahiff

(10) Patent No.: US 6,708,136 B1
(45) Date of Patent: Mar. 16, 2004

(54) ELECTRONIC DATA SYSTEM FOR USE WITH SPORTING IMPLIMENTS

(76) Inventor: Barbara A. Lahiff, 209 Ramapo Rd., Unit N, Garnerville, NY (US) 10923

( * ) Notice: Subject to any disclaimer, the term of this patent is extended or adjusted under 35 U.S.C. 154(b) by 0 days.

(21) Appl. No.: 10/194,865

(22) Filed: Jul. 12, 2002

(51) Int. Cl.⁷ ................................................ G04F 3/00
(52) U.S. Cl. .................... 702/177; 702/178; 368/62; 368/278; 368/281; 968/882
(58) Field of Search ................... 702/177, 178, 702/140, 141, 176; 324/557; 368/62–72, 278, 281, 276, 10; 473/219–226; 968/446, 452, 351, 882

(56) References Cited

U.S. PATENT DOCUMENTS

| 3,635,190 A | | 1/1972 | Araki | |
|---|---|---|---|---|
| 4,281,389 A | * | 7/1981 | Smith | 702/178 |
| 4,652,141 A | * | 3/1987 | Arai | 368/278 |
| 4,922,850 A | | 5/1990 | Conley | |
| 5,088,072 A | * | 2/1992 | Fitzmorris | 368/69 |
| 5,600,250 A | * | 2/1997 | Thompson | 324/557 |
| 5,730,658 A | | 3/1998 | Kurtz et al. | |
| 5,871,406 A | * | 2/1999 | Worrell | 473/221 |

* cited by examiner

Primary Examiner—John Barlow
Assistant Examiner—Hien Vo

(57) ABSTRACT

An electronic data system for use with sporting impliments for providing a user with an electronic device integrated into sport gloves to perform various functions unique to that particular sport. The electronic data system for use with sporting impliments includes a glove member designed for substantially enveloping a hand of a user. The glove member has a notch portion in a back side of the glove member. The notch portion is for facilitating insertion and removal of the user's hand from the glove member. The glove member has a tab portion positioned adjacent to a first side of the notch portion. A data assembly has a housing. The housing is operationally coupled to the glove member. The data assembly has a display for presenting a visual representation of information to the user.

7 Claims, 5 Drawing Sheets

ELECTRONIC DATA SYSTEM FOR USE WITH SPORTING IMPLIMENTS

BACKGROUND OF THE INVENTION

1. Field of the Invention

The present invention relates to score keeping devices and more particularly pertains to a new electronic data system for use with sporting impliments providing a user with an electronic device integrated into sport gloves to perform various functions unique to that particular sport.

2. Description of the Prior Art

The use of score keeping devices is known in the prior art. U.S. Pat. No. 3,635,190 describes a swing counter attached to the back of a golf glove and is provided for general interest in the art. Another type of score keeping device is U.S. Pat. No. 4,922,850 describing a golf glove with a stroke counting dial incorporated into a back portion. U.S. Pat. No. 5,730,658 describes a golf scoring device comprised of a rotary numbered disk, fastened to the back of a glove with a Velcro fabric.

While these devices fulfill their respective, particular objectives and requirements, the need remains for a device that includes a four digit electronic clock and golf swing counter for attachment to the back of a glove with a Velcro fastener as described.

SUMMARY OF THE INVENTION

The present invention meets the needs presented above by incorporating the above mentioned features.

Another object of the present invention is to provide a new electronic data system for use with sporting impliments that could be adapted to be utilized in other sports such as bicycling, weightlifting, and mountain climbing.

Still another object of the present invention is to provide a new electronic data system for use with sporting impliments that would be comfortable for the user to wear while providing convenient access to the controls.

To this end, the present invention generally comprises a glove member designed for substantially enveloping a hand of a user. The glove member has a notch portion in a back side of the glove member. The notch portion is for facilitating insertion and removal of the user's hand from the glove member. The glove member has a tab portion positioned adjacent to a first side of the notch portion. A data assembly has a housing. The housing is operationally coupled to the glove member. The data assembly has a display for presenting a visual representation of information to the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
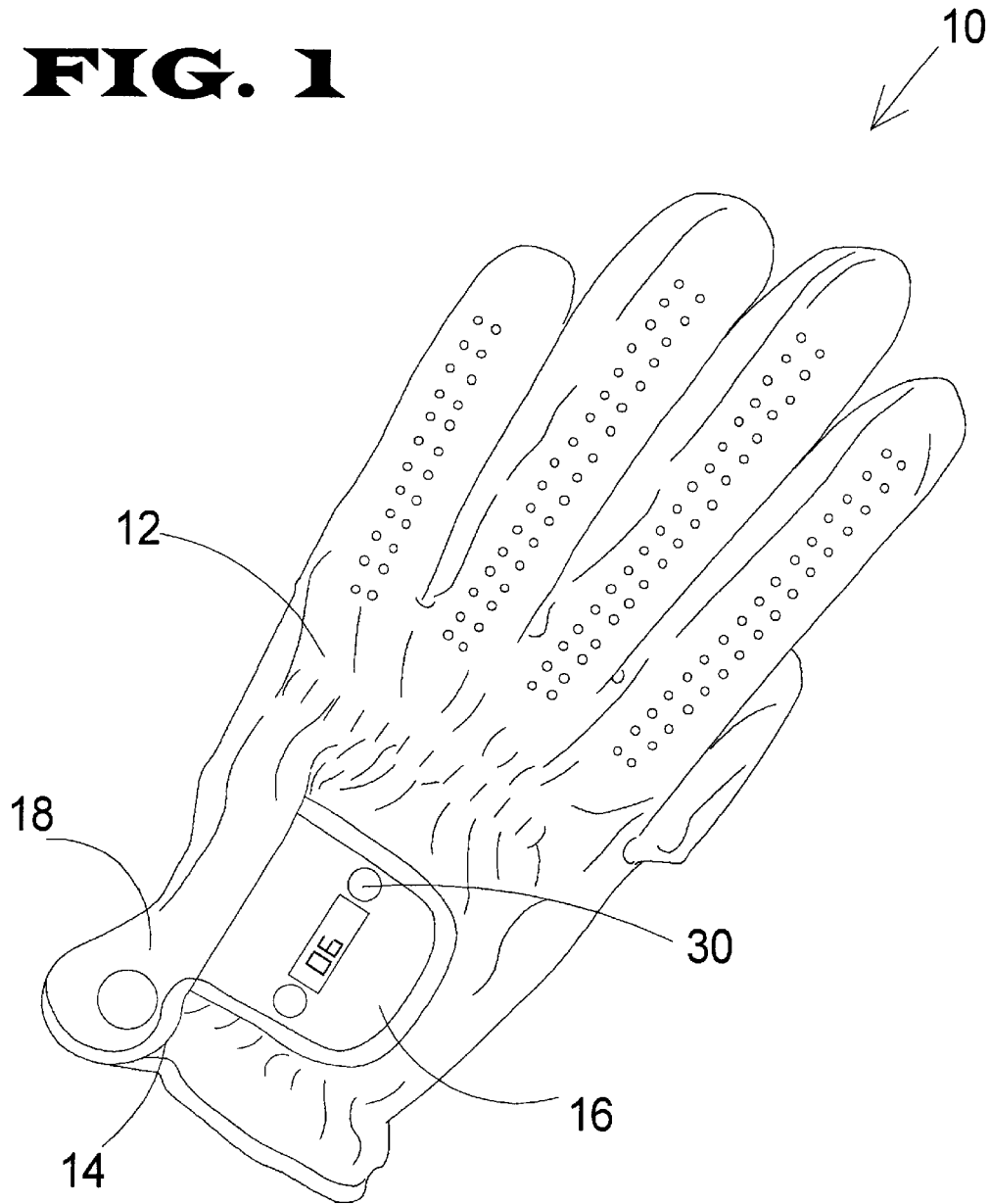
FIG. 1 is a front view of a new electronic data system for use with sporting impliments according to the present invention.
Figure 2:
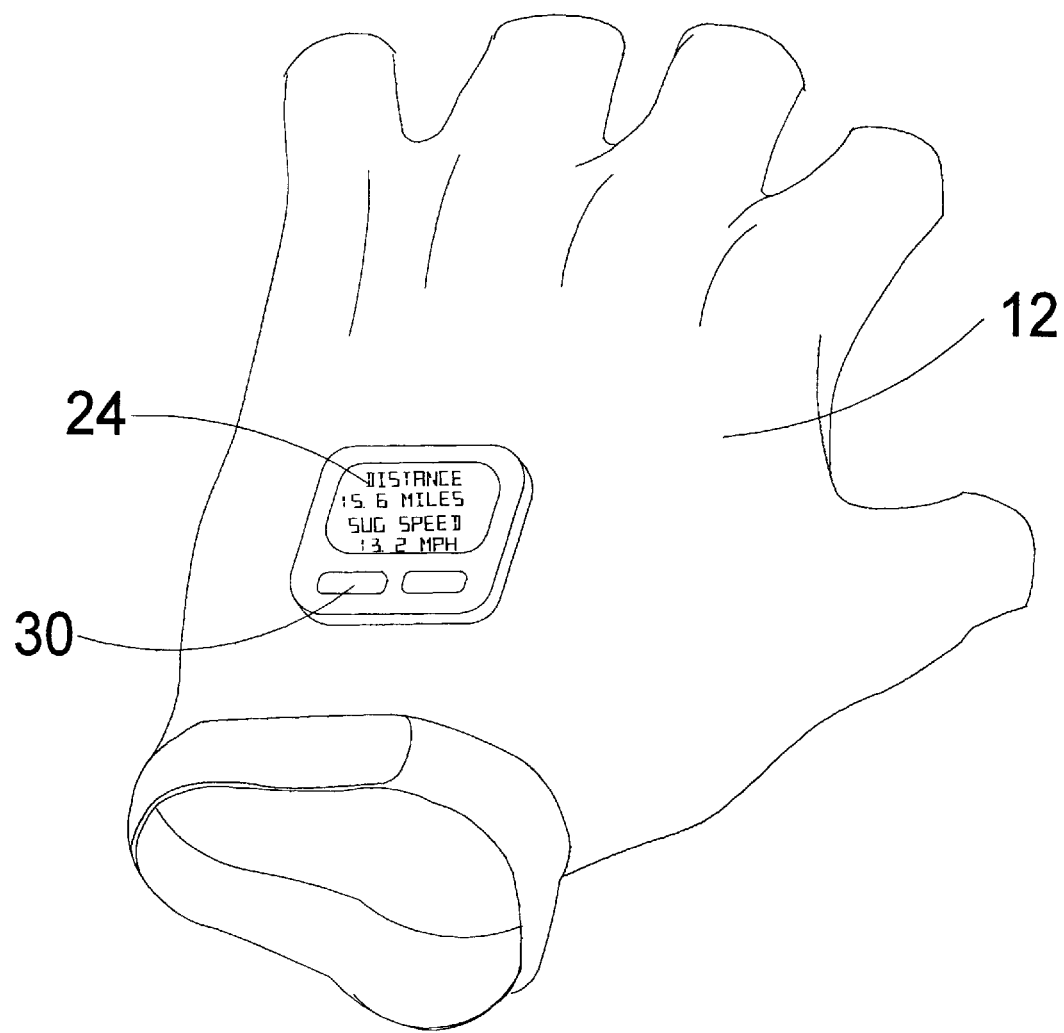
FIG. 2 is a front view of the present invention.
Figure 3:
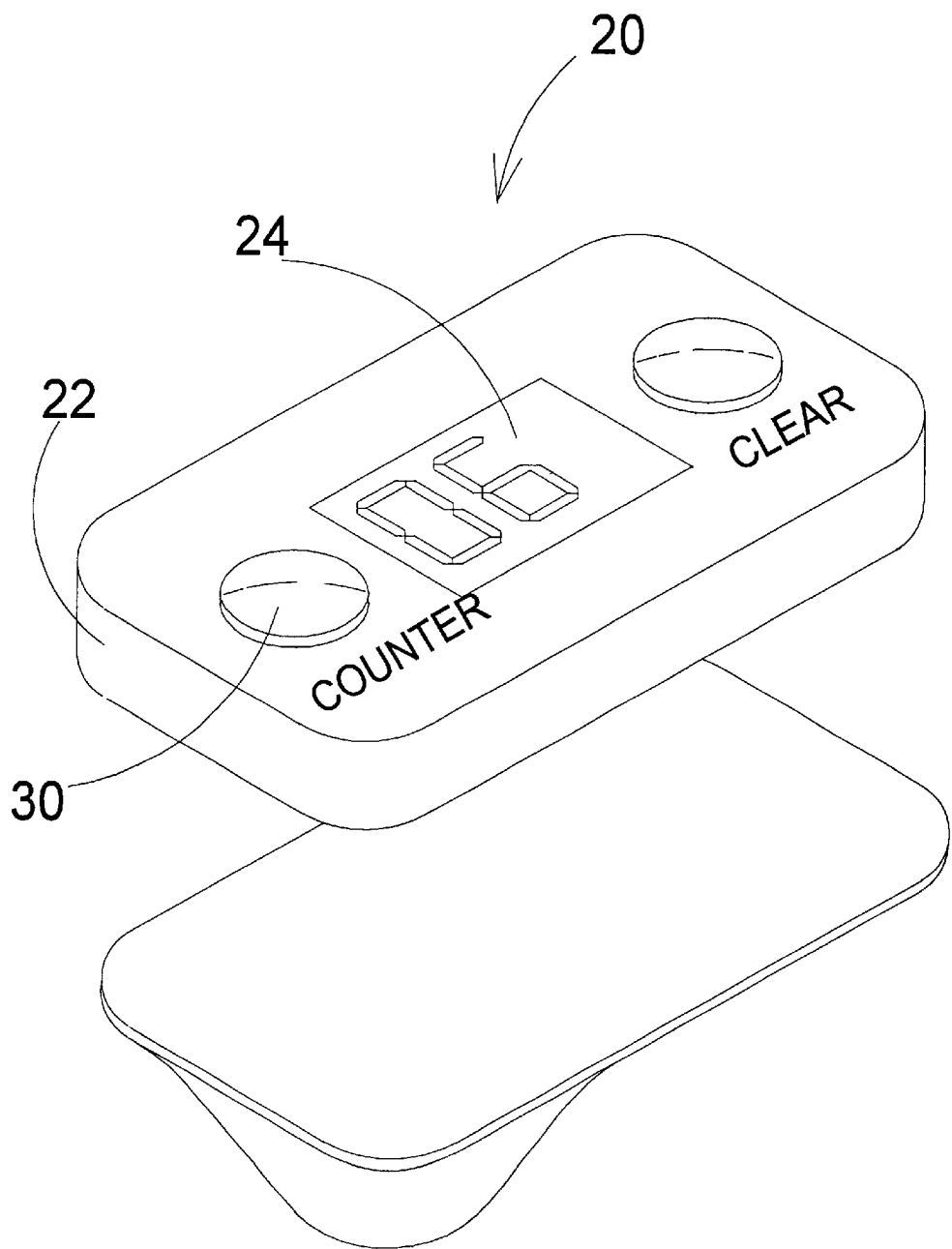
FIG. 3 is a perspective view of the present invention.
Figure 4:
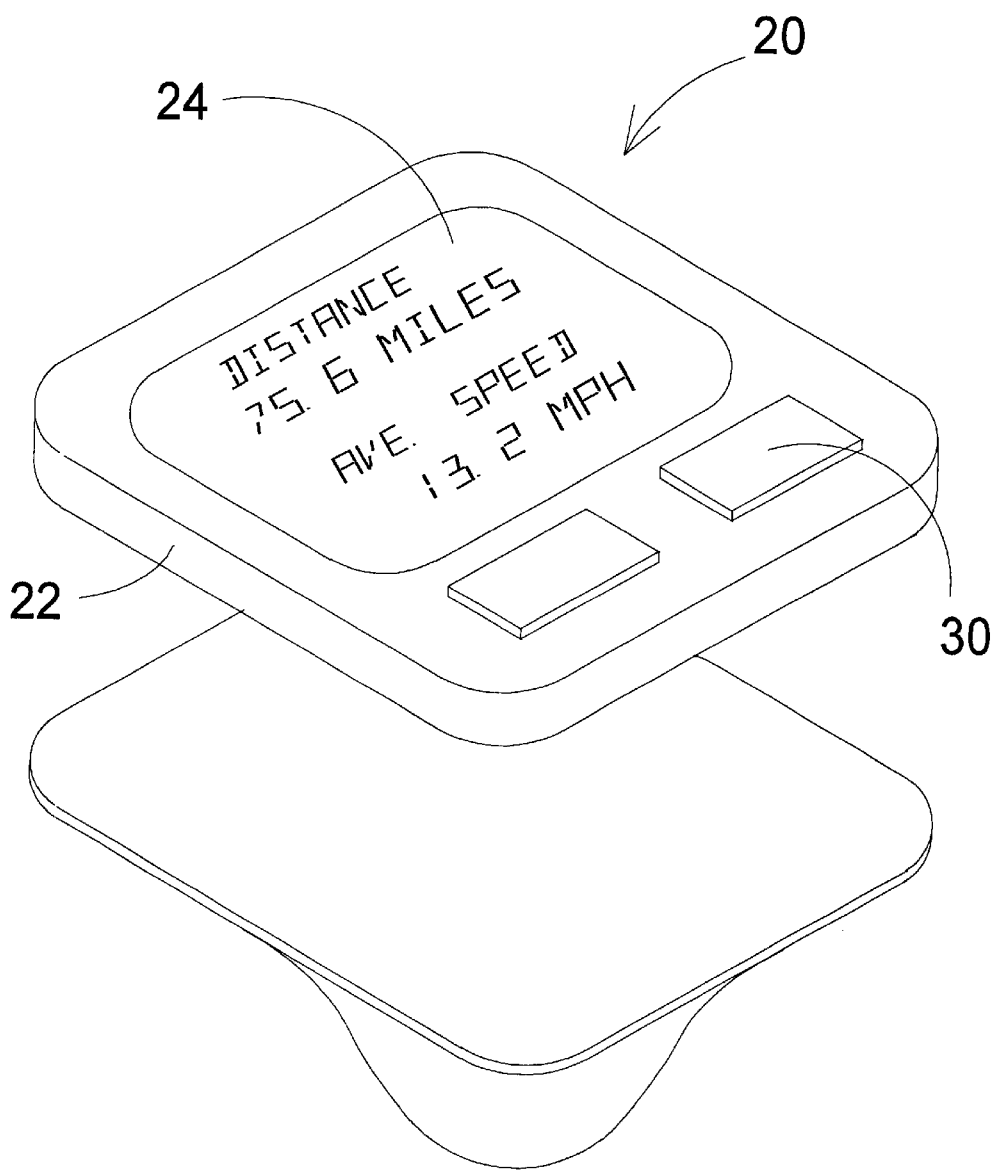
FIG. 4 is a perspective view of the present invention.
Figure 5:
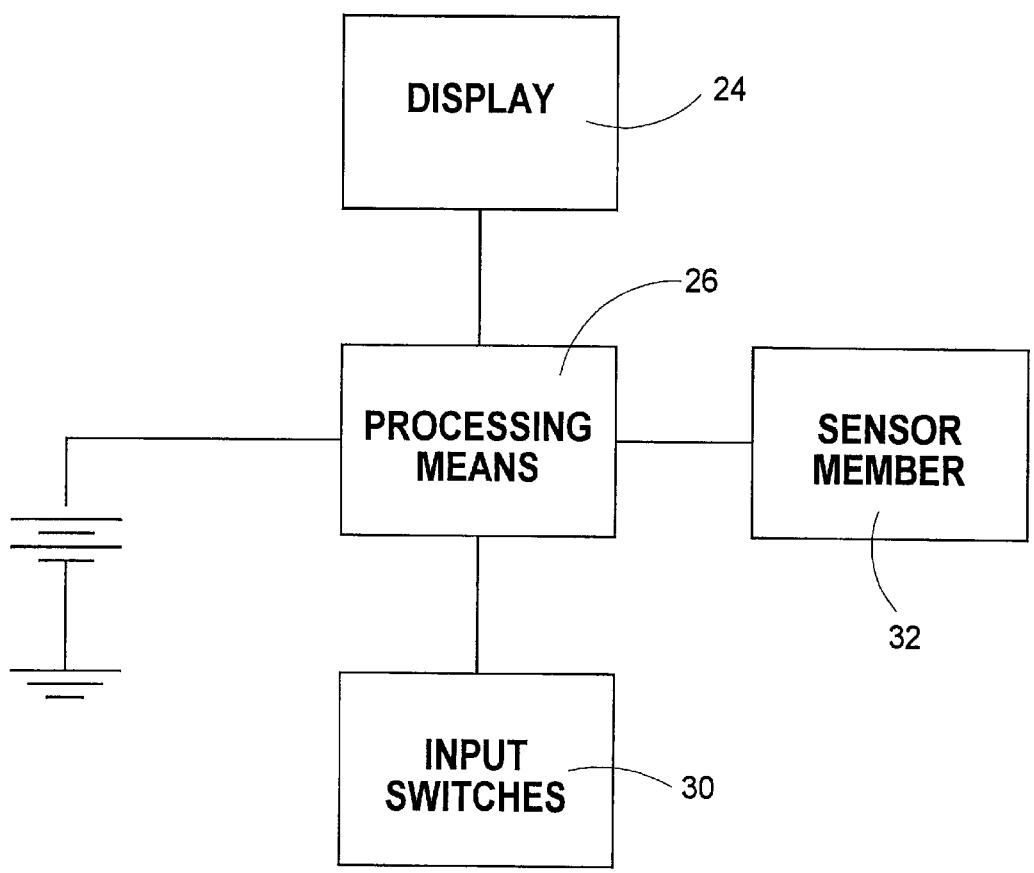
FIG. 5 is a block-diagram view of the present invention.

With reference now to the drawings, and in particular to FIGS. 1 through 5 thereof, a new electronic data system for use with sporting impliments embodying the principles and concepts of the present invention and generally designated by the reference numeral 10 will be described.

As best illustrated in FIGS. 1 through 5, the electronic data system for use with sporting impliments 10 generally comprises a glove member 12 designed for substantially enveloping a hand of a user. The glove member 12 has a notch portion 14 in a back side of the glove member 12. The notch portion 14 is for facilitating insertion and removal of the user's hand from the glove member 12. The glove member 12 has a tab portion 16 positioned adjacent to a first side 18 of the notch portion 14. A data assembly 20 has a housing 22. The housing 22 is operationally coupled to the glove member 12. The data assembly 20 has a display 24 for presenting a visual representation of information to the user.

The data assembly 20 further includes a processing means 26 for processing information to be presented to the user. The processing means 26 is positioned within the housing 22. The processing means 26 is operationally coupled to the display 24. The processing means 26 is for counting a number of strokes for each hole played during a round of golf. The processing means 26 is for calculating a time. A battery assembly 28 is positioned within the housing 22. The battery assembly 28 is operationally coupled to the processing means 26. The battery assembly 28 provides electrical energy for the processing means 26. A plurality of input switches 30 is for facilitating input of information from the user to the processing means 26. Each one of the plurality of input switches 30 is accessible through the housing 22. A sensor member 32 designed for abutting skin of the user. The senor member 32 is operationally coupled to the processing means 26. The sensor member 32 facilitating input of biometric information from the user to the processing means 26.

In use, a user would utilize the present invention similarly to a golf glove. A built in data assembly would track the stroke count by hole with total score and keep track of the time.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An electronic data system for use in conjunction with sporting activities comprising:

a glove member adapted for substantially enveloping a hand of a user, said glove member having a notch portion in a back side of said glove member, said notch portion being for facilitating insertion and removal of the user's hand from the glove member, said glove member having a tab portion positioned adjacent to a first side of said notch portion;

a data assembly having a housing, said housing being operationally coupled to said glove member, said data assembly being positioned adjacent to a back of the hand of the user and substantially aligned with a middle finger of the user, said data assembly having a display for presenting a visual representation of information to the user.

2. The system of claim 1 wherein said data assembly further comprises:

a processing means for processing information to be presented to the user, said processing means being positioned within said housing, said processing means being operationally coupled to said display;

a battery assembly positioned within said housing, said battery assembly being operationally coupled to said processing means, said battery assembly providing electrical energy for said processing means;

a plurality of input switches for facilitating input of information from the user to said processing means, each one of said plurality of input switches being accessible through said housing.

3. The system of claim 2, wherein said data assembly further comprises a sensor member adapted for abutting skin of the user, said senor member being operationally coupled to said processing means, said sensor member facilitating input of biometric information from the user to the processing means.

4. The system of claim 3 wherein said biometric information comprises a heart rate of the user.

5. The system of claim 2 further wherein said processing means being for counting a number of strokes for each hole played during a round of golf, said processing means being for calculating a time.

6. An electronic data system for use in conjunction with sporting activities comprising:

a glove member adapted for substantially enveloping a hand of a user, said glove member having a notch portion in a back side of said glove member, said notch portion being for facilitating insertion and removal of the user's hand from the glove member, said glove member having a tab portion positioned adjacent to a first side of said notch portion;

a data assembly having a housing, said housing being operationally coupled to said glove member, said data assembly being positioned adjacent to a back of the hand of the user and substantially aligned with a middle finger of the user, said data assembly having a display for presenting a visual representation of information to the user;

said data assembly further comprises:

a processing means for processing information to be presented to the user, said processing means being positioned within said housing, said processing means being operationally coupled to said display, said processing means being for counting a number of strokes for each hole played during a round of golf, said processing means being for calculating a time;

a battery assembly positioned within said housing, said battery assembly being operationally coupled to said processing means, said battery assembly providing electrical energy for said processing means;

a plurality of input switches for facilitating input of information from the user to said processing means, each one of said plurality of input switches being accessible through said housing; and a sensor member adapted for abutting skin of the user, said sensor member being operationally coupled to said processing means, said sensor member facilitating input of biometric information from the user to the processing means.

7. An electronic data system for use in conjunction with sporting activities comprising:

a data assembly having a housing, said housing being operationally couplable to a glove, said data assembly being positionable adjacent to a back of the hand of the user and substantially aligned with a middle finger of the user, said data assembly having a display for presenting a visual representation of information to the user;

said data assembly further comprises:

a processing means for processing information to be presented to the user, said processing means being positioned within said housing, said processing means being operationally coupled to said display, said processing means being for counting a number of strokes for each hole played during a round of golf, said processing means being for calculating a time;

a battery assembly positioned within said housing, said battery assembly being operationally coupled to said processing means, said battery assembly providing electrical energy for said processing means;

a plurality of input switches for facilitating input of information from the user to said processing means, each one of said plurality of input switches being accessible through said housing; and a sensor member adapted for abutting skin of the user, said sensor member being operationally coupled to said processing means, said sensor member facilitating input of biometric information from the user to the processing means.

* * * * *